(12) United States Patent
Tashima et al.

(10) Patent No.: US 6,241,773 B1
(45) Date of Patent: Jun. 5, 2001

(54) BIOMEDICAL ARTICLE MADE OF ALUMINA CERAMICS

(75) Inventors: Syunzo Tashima, Apt. No. 501, Barumii-Yokogawa, 7-7, Yokogawasho 1-chome, Nishi-ku, Hiroshima, Hiroshima-ken; Toshihiko Shimotoso, Shiga-ken; Yoshio Taniguchi, Omihachiman, all of (JP)

(73) Assignees: Kyocera Corporation, Tyoto; Syunzo Tashima, Hiroshima, both of (JP)

( * ) Notice: Subject to any disclaimer, the term of this patent is extended or adjusted under 35 U.S.C. 154(b) by 0 days.

(21) Appl. No.: 09/342,016

(22) Filed: Jun. 28, 1999

(30) Foreign Application Priority Data

Jun. 30, 1998 (JP) .................................................. 10-185027

(51) Int. Cl.⁷ ........................................................ A61F 2/36
(52) U.S. Cl. ............................................................ 623/23.56
(58) Field of Search .............................. 623/16.11, 19.11, 623/20.16, 23.56–23.59

(56) References Cited

U.S. PATENT DOCUMENTS

| | | | |
|---|---|---|---|
| 3,919,723 | 11/1975 | Heimke et al. | |
| 4,012,795 | * 3/1977 | Doore et al. | 3/1.91 |
| 4,016,651 | 4/1977 | Kawahara et al. | |
| 4,032,994 | * 7/1977 | Frey | 3/1.912 |
| 4,538,306 | * 9/1985 | Dorre et al. | 623/20 |
| 4,950,294 | 8/1990 | Hakamatsuka | |
| 4,954,080 | * 9/1990 | Kelly et al. | 433/8 |
| 5,352,643 | * 10/1994 | Staehler et al. | 501/127 |

FOREIGN PATENT DOCUMENTS

| | | |
|---|---|---|
| 834985 | * 4/1976 | (BE) . |
| 1334584 | 10/1973 | (GB) . |
| 1472311 | 5/1977 | (GB) . |
| 1-040058 | 2/1989 | (JP) . |
| 5-065504 | 3/1993 | (JP) . |
| 6-293010 | 10/1994 | (JP) . |
| 9528364 | 10/1995 | (WO) . |

* cited by examiner

Primary Examiner—David H. Willse
Assistant Examiner—Hieu Phan
(74) Attorney, Agent, or Firm—Hogan & Hartson, LLP

(57) ABSTRACT

A biomedical article made of alumina ceramics including an aluminum oxide having a purity of not less than 99.95% and unavoidable impurities as remainder. The alumina ceramics contains no sintering agent. The alumina ceramics has no irregularities in the crystal grain size, and has a strength necessary for biomedical article, and have a crystal grain size of less than 1.0 μm to assure excellent slidability.

7 Claims, 3 Drawing Sheets

BIOMEDICAL ARTICLE MADE OF ALUMINA CERAMICS

This application is based on patent application No. 10-185027 filed in Japan, the contents of which are hereby incorporated by reference.

BACKGROUND OF THE INVENTION

1. Field of the Invention

This invention relates to a biomedical article made of alumina ceramics and, more particularly, to an alumina ceramics biomedical article having a high strength and an excellent slidability.

2. Description of the Prior Art

As artificial bone members such as artificial hip joint, there have been known an artificial hip joint comprising a combination of a polymer material (e.g., ultra-high molecular weight polyethylene). However, there has been the problem that the long use of the socket made of ultra-high molecular weight polyethylene in the living body causes a wear of the socket, resulting in a displacement between the implanted artificial bones and the natural bones in the living body due to wear powder. Also, wear powder of metal has been worried to give adverse influence to the living body. Further, zirconia ceramics is subject to crystalline phase transference phenomenon in a long use, consequently lowering the mechanical strength.

To solve these problems, a variety of research and development about artificial bone members have been made. As an example, use of alumina ceramics has been proposed because of harmless to the human body.

Japanese Laid Open Patent Application No. 51-67693 discloses a stem head made of alumina ceramics comprising an aluminum oxide having a purity of not less than 99.7% by weight, a density of not less than 3.90 g/cm$^3$, and an average crystal grain size of not more than 10 $\mu$m. This artificial bone member can reduce the wear of a socket made of ultra-high molecular weight polyethylene. However, its mechanical strength is insufficient.

Japanese Patent No. 2579212 discloses a stem head made of polycrystalline alumina ceramics comprising an aluminum oxide having a purity of from 99.5 to 99.9% by weight and an oxide of at least one selected from the group consisting of Mg, Ca, Ba, Sr, Sc, Y, La and Ce as sintering agent. Also, Japanese Patent Publication No. 7-94344 discloses a stem head made of polycrystalline alumina ceramics comprising an aluminum oxide having a purity of not less than 99.9% by weight and an oxide of at least one selected from the group consisting of Mg, Ca, Ba, Sr, Sc, Y, La and Ce as sintering agent.

However, these known artificial bone members have the following problems. The alumina ceramics constituting the artificial bone member include the sintering agent. The sintering agent causes glassy grain boundary layers in a sintered body, accordingly making it impossible to raise the three-point bending strength of the alumina ceramics more than 640 MPa, which is considerably lower than zirconia ceramics having a strength of about 1200 MPa. Accordingly, the artificial bone member made of such alumina ceramics is likely to break or fracture in the living body.

On the other hand, reducing the addition of sintering agent involves a poor dispersion of sintering agent, resulting in partial crystal grain size increases because of insufficient deterrent to crystal grain growth, and thus irregularities in the crystal grain size of the sintered body. Consequently, the mechanical strength of the alumina ceramics lowers.

The artificial bone member made of alumina ceramics has an improved slidability to a socket made of ultra-high molecular weight polyethylene. From the viewpoint of reduction or elimination of wear powder, it could be thought to be advantageous to combine an artificial joint made of ceramics and an artificial socket made of ceramics because of the high hardness of ceramics. However, there have never been raised any technical proposals of improved alumina ceramics having excellent slidability especially at a ceramics to ceramics interface to take such advantageous effect of alumina ceramics. This subject demands close investigation for biomedical articles.

SUMMARY OF THE INVENTION

It is an object of the present invention to provide an artificial biomedical article which has overcome the problems residing in the prior art.

It is another object of the present invention to provide an artificial biomedical article made of alumina ceramics which has substantially the same mechanical strength (three-point bending strength) as zirconia ceramics, and exhibits not only excellent slidability to an article made of ultra-high molecular weight polyethylene, but also excellent slidability to an article made of alumina ceramics.

According to an aspect of the present invention, a biomedical article is made of alumina ceramics comprising an aluminum oxide having a purity of not less than 99.95% and unavoidable impurities as remainder. The alumina ceramics contain no sintering agent, and have a density of not less than 3.94 g/cm$^2$.

This biomedical article can be used as an artificial joint member which requires a high strength and a high slidability. The alumina ceramics have substantially the same strength as zirconia ceramics, and maintain the required strength for a prolonged period of time. Accordingly, the alumina ceramics can also be used as an artificial bone and a bone-reinforcing member, in addition to the joint member.

DETAILED DESCRIPTION OF PREFERRED EMBODIMENTS OF THE INVENTION

Figure 1:
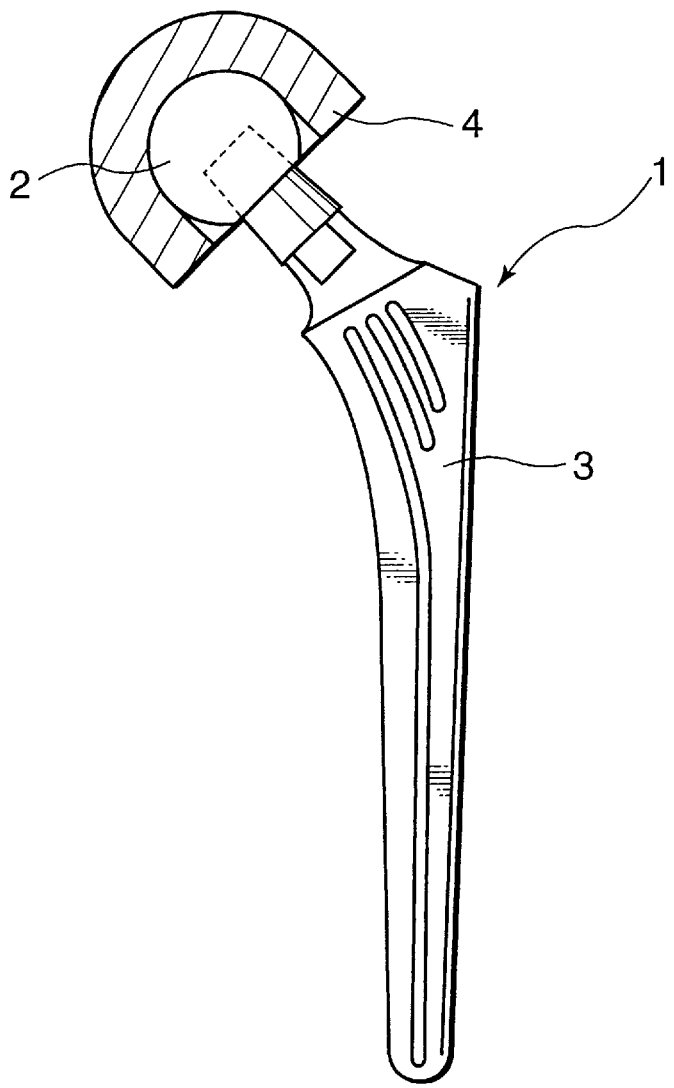
FIG. 1 is a partially sectional sideview of an artificial hip joint which employs a stem head and a socket according to an embodiment of the invention.

Alumina ceramics for an biomedical article of present invention comprises an aluminum oxide having a purity of not less than 99.95% and unavoidable impurities. However, any sintering agent is not added. The alumina ceramics have an average crystal grain size of not more than 1 μm, and a density of not less than 3.94 g/cm³.

In the case that the content of the aluminum oxide is less than 99.95% by weight, the content of the unavoidable impurities is greater, which consequently causes formation of grain boundary layers and decreases the mechanical strength. Therefore, the content of the aluminum oxide is required to be not less than 99.95% by weight. In the case that the content of the unavoidable impurities is not more than 0.05% by weight, there is few formation of grain boundary layer. Accordingly, a high mechanical strength can be attainable.

The average crystal grain size is required to be not more than 1 μm. Such an average crystal grain size ensures a smooth sliding surface of the alumina ceramics, thereby making it possible to effectively eliminate occurrence of wear powder. If the average crystal grain size exceeds 1 μm, grain particles are liable to be worn off from the sliding surface, consequently impairing the slidability.

Furthermore, any sintering agent is not added in the alumina ceramics constituting the biomedical article of present invention. No addition of any sintering agent can eliminate the likelihood of irregularities in the crystal grain size, which are caused by addition of sintering agent and lower the strength of alumina ceramics or sintered body.

The alumina ceramics contains no sintering agent. Specifically, an oxide or oxides of Mg, Ca, Ba, Sr, Sc, Y, La, and Ce are not substantially contained in the alumina ceramics. However, the alumina ceramics contains an oxide of Si, Fe, and K as unavoidable impurities. Further, there should be noted to be a possibility that the alumina ceramics contains an oxide of Mg and Ca as unavoidable impurities to a neglectable amount because they usually exist in the natural world. Even in the case of containing such oxide as unavoidable impurities, however, the content of each of magnesium oxide and calcium oxide does not exceed 100 ppm. Accordingly, existence of magnesium oxide or calcium oxide should be considered as unavoidable impurities of the alumina ceramics as far as not exceeding 100 ppm because each of these oxides does not give adverse effect to the strength of the alumina ceramics at not more than 100 ppm. These unavoidable impurities are measured by use of an ICP emission spectrochemical analyzer.

The density of the alumina ceramics is not less than 3.94 g/cm³, and more preferably not less than 3.96 g/cm³. If the density of the alumina ceramics is less than 3.94 g/cm³, a number of pores occur in the alumina ceramics, consequently lowering the mechanical strength.

Furthermore, the alumina ceramics have a mechanical strength (three-point bending strength) of not less than 600 MPa, and more preferably not less than 750 MPa, to reliably prevent breakage or fracture in the living body.

The alumina ceramics may be produced in the following steps. To ultra-fine powder of aluminum oxide which has a purity of not less than 99.99% by weight and an average particle diameter of 0.21 μm are added a solvent (e.g., ion-exchanged water), a binder (e.g., acrylic polymer) and a dispersing agent (e.g., polycarboxylic acid ammonium salt) to prepare a mixture. The mixture is sufficiently mixed by a rotary mill, and then deaerated in vacuum to prepare a slurry. The slurry is poured into a gypsum mold to obtain a compact having a desired shape, which is in turn sintered at a temperature of 1200° C. to 1450° C. for 2 hours to produce a polycrystalline alumina ceramics.

Alternatively, to an ultra-fine powder of aluminum oxide which has a purity of not less than 99.99% by weight and an average particle diameter of 0.15 μm are added a solvent (e.g., ultra purity water), a binder (e.g., acrylic polymer) and a dispersing agent (e.g., polycarboxylic acid ammonium salt) to prepare a mixture. The mixture is sufficiently mixed by a rotary mill, and then deaerated in vacuum to prepare a slurry. The slurry is placed in a mold. The mold is set in a centrifugal machine to form a compact by a centrifugal force of not less than 3,000 G. The resulting compact is dried and then sintered at a temperature of 1200° C. to 1450° C. for 2 hours to obtain polycrystalline alumina ceramics.

Next, a detailed description will be made on embodiments of the present invention with reference to accompanying drawings.

FIG. 1 shows a partially sectional sideview of an artificial hip joint which employs a stem head and a socket member. Indicated at 1 is an artificial hip joint member comprising a metal stem 3 to be inserted into the femoral medullary cavity, and a stem head 2 mounted on a tip of the stem 3. The head ball 2 is connected with the stem 3 by a pin. The head ball 2 is made of the above-mentioned alumina ceramics comprising aluminum oxide having a purity of not less than 99.95% and an unavoidable impurities as remainder. The alumina ceramics has an average crystal grain size of not more than 1 μm. However, the alumina ceramics contains no sintering agent.

Indicated at 4 is a socket which is made of the above-mentioned alumina ceramics and is provided at the acetabulum. The socket 4 may be made of an ultra-high molecular weight polyethylene. The head ball 2 is rotatable on the socket 4.

The head ball 2 is made as follows. A mixture is prepared which contains alumina powder of aluminum oxide having a purity of 99.99% by weight and an average particle diameter of 0.22 μm (Taimicron TM-DAR, produced by Taimei Chemicals Co., Ltd.), ion-exchanged water as a solvent, acrylic polymer as a binder and polycarboxylic acid ammonium salt as a dispersing agent. The mixture is sufficiently mixed by means of a rotary mill, and then deaerated in vacuum to prepare a slurry. The slurry is poured into a gypsum mold having an inner shape corresponding to the shape of the head ball 2 to prepare a compact. The compact is sintered at a temperature of 1250° C. for 2 hours to produce the head ball 2. The sintered alumina ceramics has 99.97% by weight of alumina oxide and an average crystal grain size of 0.8 μm.

Alternatively, it may be possible to place the above-prepared slurry in a mold having a shape corresponding to the shape of the head ball 2, and set the mold filled with the slurry in a centrifugal machine to prepare a consolidated compact having the specified shape by a centrifugal force of 10 to 20 kG. The resulting consolidated compact is dried at 40° C. for 4 hours, and at 100° C. for 4 hours, and put in an air furnace and heated at a rate of 120° C./hour, and then degreased at 500° C. for 1 hour. Subsequently, the compact was heated at a rate of 200° C./hour, temporarily fired at 800° C. for 1 hour and then properly fired at 1250° C. for 2 hours to produce the head ball 2.

In the case where the content of the aluminum oxide is less than 99.95%, or the average crystal grain size exceeds 1 μm, there is the fear that the wear loss considerably increases.

The alumina ceramics forming the biomedical article of the present invention has excellent slidability as will be seen from the following example. Accordingly, such alumina ceramics may be used for an artificial bone, a bone-reinforcing member, and the like, which are subject to high load because the mechanical strength of the alumina ceramics is a match for that of zirconia ceramics.

Figure 2:
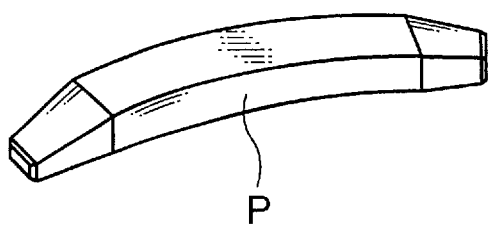
FIG. 2 is a perspective view showing a pin for rib bonding according to another embodiment of the invention.
Figure 3:
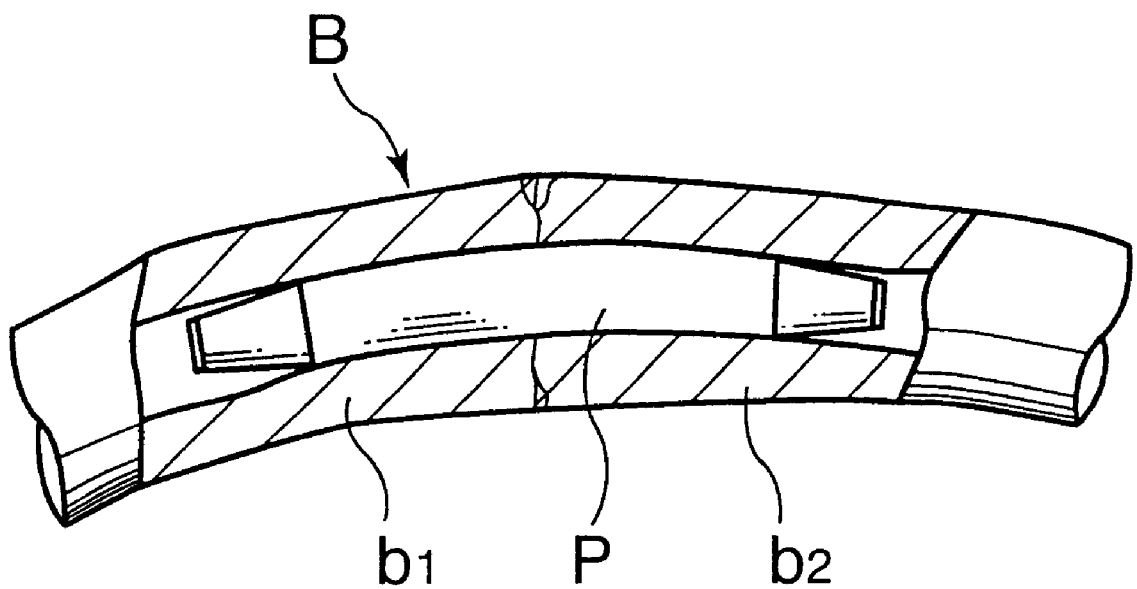
FIG. 3 is a partially sectional view showing a fractured rib inserted with the pin shown in FIG. 2.

FIG. 2 to FIG. 3 shows a pin for use in a rib as another embodiment of the present invention. Indicated P is a pin for restoring a fractured or broken rib. Specifically, as shown in FIG. 3, the pin P having a size suited for the rib medullary cavity of a broken portion is inserted into a fractured rib B. The broken bone pieces are fixedly connected with each other by a wire (not shown), thereby bonding the broken bone pieces b1 and b2. The pin P is made of the alumina ceramics comprising an aluminum oxide having a purity of not less than 99.95% and an unavoidable impurities as remainder, and having a density of not less than 3.94 g/cm$^3$, but containing no sintering agent. This alumina ceramics constituting the pin P has the mechanical strength equivalent of the zirconia ceramics, as described above. Accordingly, the pin P is resistible to a large load.

Two embodiments of the present invention have been described as above, but the present invention is not limited to such embodiments. It will be appreciated that the present invention may be embodied in any forms without departing from the scope of the appending claims. For example, the present invention may be widely applied as artificial members constituting a leg joint portion, other bones, bone reinforcing members or the like.

EXAMPLE

Sample Nos. 1 to 11 were produced by mixing alumina powder having a specified weight percent of aluminum oxide, polycarboxylic acid ammonium salt as a dispersant, acrylic polymer as an organic binder, and water with one another by a rotary mill to prepare a slurry, placing the slurry in a mold having a specified shape, and applying a centrifugal force of 15,000 G to the slurry placed in the mold to make a compact, taking out the compact from the mold, and sintering the compact at a temperature of 1200° C. to 1500° C. for 2 hours. Sample Nos. 12 to 16 were produced by preparing the slurry in a similar manner to the preparation of the slurry for Sample Nos. 1 to 11, pouring the slurry into a gypsum mold having a specified shape, and sintering it at a temperature of 1250° C. for 2 hours. However, Sample Nos. 12 to 16 were added with a sintering agent of MgO, although Sample Nos. 1 to 11 were not added with the sintering agent of MgO. The respective contents of aluminum oxide, sintering agent, and unavoidable impurity of Sample Nos. 1 to 16 are shown in Table 1.

Each Sample was grounded by a diamond grinder into a size of 3 mm×4 mm×40 mm. The bending strength of each Sample was measured by the bending test specified in JIS (JAPANESE INDUSTRIAL STANDARDS)-R-1601. The average crystal grain size of each Sample was measured in accordance with ASTM-E112, and its density was measured in accordance with JIS-C-2141. To evaluate the wear loss of each Sample, further, a wear test was carried out for each Sample by pin-on-disk test apparatus which is described below. The results are shown in Table 1.

In the wear test, there was prepared a set of a pin test piece and a disk test piece for each sample. The pin test piece was formed into a slender shape having an outer diameter of 6 mm. Also, the pin test piece was formed with a spherical portion having a radius of 500 mm at the tip. The tip portion of the pin test piece and the disk test piece are abrasive-finished to the same degree as that in the case of the sliding surface of a stem head of an artificial hip joint. The disk test piece was formed into a hollow cylinder having an outer diameter of 40 mm, an inner diameter of 20 mm, and a thickness of 9 mm. The pin test piece and the disk test piece were made of the same alumina ceramics specified for each sample.

Figure 4:
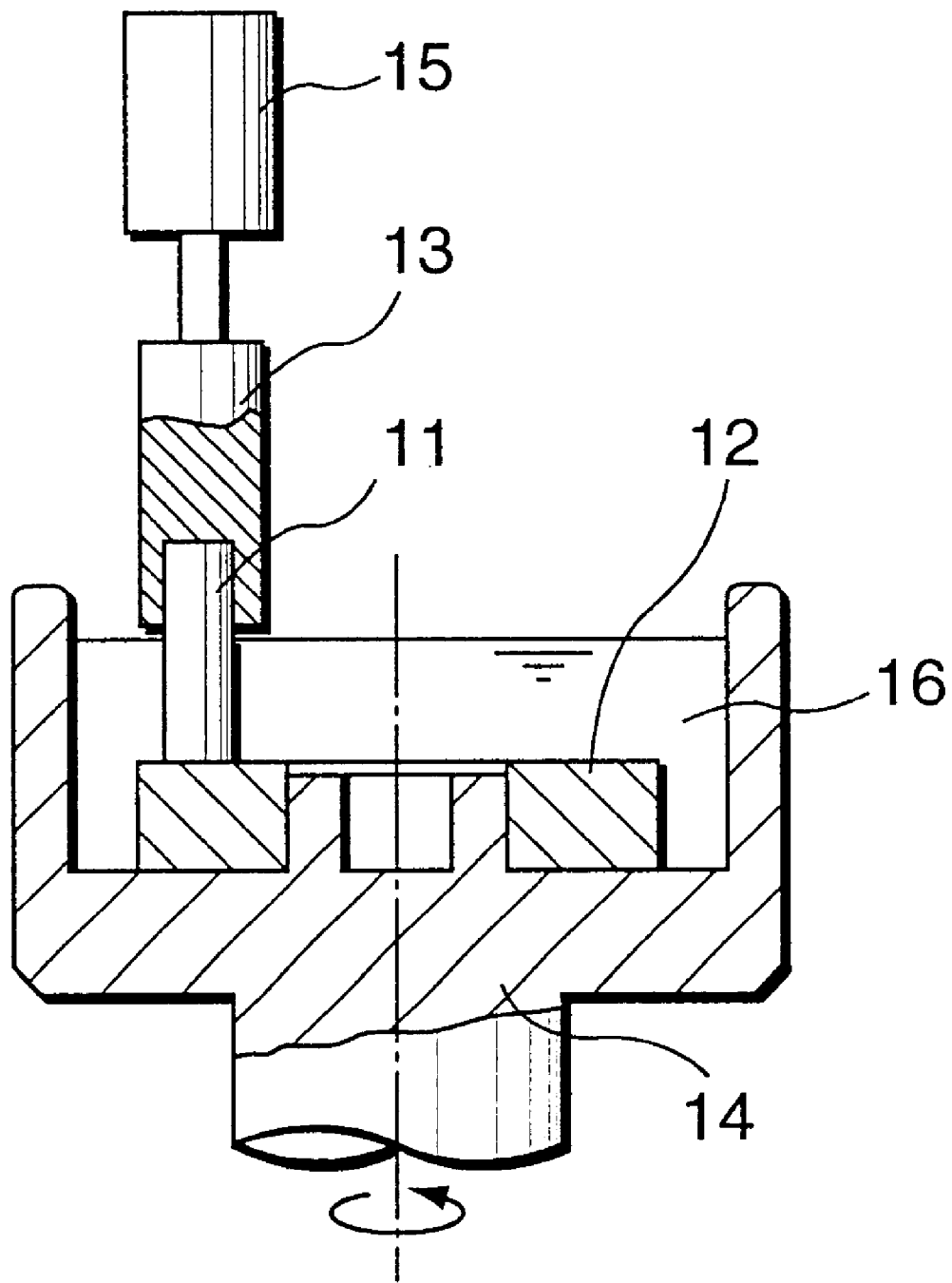
FIG. 4 is a sectional view showing a construction of pin-on-disk test apparatus used for measuring the wear loss of ceramics samples.

The construction of the pin-on-disk wear loss measuring apparatus used in this example is briefly illustrated in FIG. 4. The apparatus includes a rotary holder 14 and a stationary holder 13 provided above the rotary holder 14. The rotary holder 14 has an opened chamber in which a disk-shaped test piece 12 is set and a lubricant liquid 16 is placed. The rotary holder 14 is rotated at a specified speed. The stationary holder 13 is adapted for holding a pin-shaped test piece 12. The stationary holder 13 is mounted with a load member 15 to ensure contact of the pin-shaped test piece 11 with the disk-shaped test piece 12 at a constant pressure. In this apparatus, a wear loss is measured by calculating a difference between a weight of an original test piece and a weight of a worn test piece. In other words, the weight difference is defined as a wear loss of the test piece.

In the wear test, distilled water was added as a lubricating solution and a contact load of 210 N was applied to the contact surface, and then the sample was slid by 30,000 m at a sliding rate of 40 mm/second. After the completion of the wear test, the weight of the pin was measured again to determine a specific wear quantity.

Chemical analysis of the sintering agent and the unavoidable impurities was conducted by ICP emission spectrochemical analysis and atomic spectrometry. The content of the alumina ceramics was obtained by subtracting a measured total weight of the sintering agent and the unavoidable impurities from the whole weight of the ceramics.

TABLE 1

| Sample No. | Content of alumina (%) | Content of sintering agent (%) | Content of unavoidable impurities (%) | Average crystal grain size (μm) | Density (g/cm³) | Wear loss of Pin (mm³/Nm) | Bending strength (MPa) |
|---|---|---|---|---|---|---|---|
| 1 | 99.98 | None | 0.02 | 0.2 | 3.95 | $0.30 \times 10^{-3}$ | 1050 |
| 2 | 99.98 | None | 0.02 | 0.4 | 3.94 | $0.60 \times 10^{-3}$ | 750 |
| 3 | 99.98 | None | 0.02 | 0.6 | 3.95 | $0.16 \times 10^{-3}$ | 1150 |
| 4 | 99.98 | None | 0.02 | 0.8 | 3.95 | $0.25 \times 10^{-3}$ | 1090 |
| 5 | 99.98 | None | 0.02 | 0.9 | 3.96 | $0.27 \times 10^{-3}$ | 990 |
| 6 | 99.97 | None | 0.03 | 0.7 | 3.95 | $0.30 \times 10^{-3}$ | 980 |
| 7 | 99.95 | None | 0.05 | 0.8 | 3.95 | $0.35 \times 10^{-3}$ | 950 |
| 8 | 99.98 | None | 0.02 | 1.2 | 3.96 | $1.15 \times 10^{-3}$ | 750 |
| 9 | 99.98 | None | 0.02 | 1.8 | 3.97 | $1.60 \times 10^{-3}$ | 600 |
| ✗10 | 99.98 | None | 0.02 | 0.2 | 3.88 | $4.60 \times 10^{-3}$ | 320 |
| ✗11 | 99.98 | None | 0.02 | 0.3 | 3.90 | $3.50 \times 10^{-3}$ | 430 |
| ✗12 | 99.92 | MgO 0.0500 | 0.03 | 0.8 | 3.94 | $6.10 \times 10^{-3}$ | 410 |
| ✗13 | 99.92 | MgO 0.0500 | 0.03 | 1.5 | 3.96 | $2.50 \times 10^{-3}$ | 650 |
| ✗14 | 99.90 | MgO 0.0500 | 0.05 | 1.8 | 3.97 | $3.30 \times 10^{-3}$ | 600 |
| ✗15 | 99.70 | MgO 0.2000 | 0.10 | 5.0 | 3.97 | $5.55 \times 10^{-3}$ | 420 |
| ✗16 | 99.50 | MgO 0.2000 | 0.30 | 8.0 | 3.95 | $10.30 \times 10^{-3}$ | 380 |

✗denotes the sample out of the invetion

As is apparent from Table 1, Sample Nos. 1 to 7 each have the excellent mechanical strength (i.e., high bending strength) as well as the excellent slidability (i.e., low wear loss) comparing to Sample Nos. 12 to 16, which contain the sintering agent. Also, Sample Nos. 1 to 7 each have better mechanical strength and slidability than Sample Nos. 10 and 11, which have the density lower than 3.94 g/cm². Sample Nos. 8 and 9, which have the average crystal grain size greater than 1.0 μm, have relatively higher wear loss than Sample Nos. 1 to 7, but have the high mechanical strength.

What is claimed is:

1. A biomedical article made of an alumina ceramic comprising:

an aluminum oxide having a purity of not less than 99.95%;

no sintering agent selected from the group consisting of oxide or oxides of barium, strontium, scandium, yttrium, lanthanum and cerium; and not more than 100 ppm calcium oxide or magnesium oxide, wherein the alumina ceramic has a wear resistance of not less than $4.60 \times 10^{-3}$ mm³/Nm on the pin-on-disk test, a three-point bending strength of not less than 600 MPa and a density of not less than 3.94 g/cm³.

2. The biomedical article according to claim 1, wherein the alumina ceramic has an average crystal grain size of not more than 1.0 μm.

3. The biomedical article according to claim 1, wherein the alumina ceramic has a three-point bending strength of not less than 750 MPa.

4. The biomedical article according to claim 1, wherein the alumina ceramic has a wear resistance having a wear loss of not more than $1.0 \times 10^{-3}$ mm³/Nm under the pin-on-disc test.

5. The biomedical article according to claim 1, wherein the biomedical article is an artificial joint.

6. The biomedical article according to claim 1, wherein the biomedical article is an artificial bone.

7. The biomedical article according to claim 1, wherein the biomedical article is an artificial bone-reinforcing member.

* * * * *